(12) United States Patent
Gehant

(10) Patent No.: US 7,662,934 B2
(45) Date of Patent: Feb. 16, 2010

(54) PROCESS FOR REDUCING BIOMASS-BIOMASS OR BIOMASS—RESIN INTERACTIONS

(75) Inventor: Richard L. Gehant, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 288 days.

(21) Appl. No.: 11/264,300

(22) Filed: Oct. 31, 2005

(65) Prior Publication Data

US 2006/0106205 A1   May 18, 2006

Related U.S. Application Data

(63) Continuation of application No. 10/655,874, filed on Sep. 5, 2003, now Pat. No. 6,967,241.

(60) Provisional application No. 60/408,653, filed on Sep. 6, 2002.

(51) Int. Cl.
  *A23J 1/00* (2006.01)
(52) U.S. Cl. ............... 530/412; 530/422; 530/350; 530/300; 435/7.1; 435/325; 435/252.1
(58) Field of Classification Search ................... None
  See application file for complete search history.

(56) References Cited

U.S. PATENT DOCUMENTS

| 4,988,798 | A | 1/1991 | Blum et al. |
| 5,760,189 | A | 6/1998 | Vicik et al. |
| 6,967,241 | B2 | 11/2005 | Gehant |
| 2002/0010145 | A1 | 1/2002 | Willson, III et al. |
| 2007/0031930 | A1 | 2/2007 | Gehant |

FOREIGN PATENT DOCUMENTS

| EP | 0 229 866 A1 | 7/1987 |
| JP | 1-502556 T | 9/1989 |
| JP | 5-503212 T | 6/1993 |
| JP | 11-509725 T | 8/1999 |
| WO | WO-87/06939 A1 | 11/1987 |
| WO | WO-88/01624 A1 | 3/1988 |
| WO | WO 96/34622 A1 * | 11/1996 |
| WO | WO 01/42456 A2 | 6/2001 |
| WO | WO-2004/022581 A1 | 3/2004 |

OTHER PUBLICATIONS

Drechsel, D., Geerlof, A., Marco, A.D., Stier, G., Weeks, S., Zandt, H., *The Protein Expression and Purification Flowerchart*, Internet Article, 'Online' Nov. 10, 2000, XP002357722 EMBL Heidelberg, URL:www.embl.ed/ExternalInfo/protein_unit/draft_frames/Frame_flowchart_ext.htm.*
"Expanded Bed Adsorption, Principles and Methods," Edition AB, pp. 1-160, 1997.
Gehant, R. et al., 2002 (Sep. 8), *EBA Conference*, Abstract, 1 pg. "Overcoming the Difficulties of Performing CEX-Expanded Bed Chromatography with Low pH *E. coli* Homogenates".
Harris, E. et al. (Ed.), "Protein purification methods, a practical approach," pp. 1-22; Sep. 1, 1990.
Nye, S. et al., 1995, *Molecular Immunology*, vol. 32, No. 14/15, pp. 1131-1141 "Purification of Immunologically Active Recombinant 21.5 kDa Isoform of Human Myelin Basic Protein".
Wheelwright, S., "Protein Purification, Design and Scale up of Downstream Processing," Chapter 5 and 6, 11 pgs., 1991, John Wiley & Sons Inc, New York pp. 52-81.
International Search Report mailed on Feb. 11, 2004, for PCT Application No. PCT/US03/28007, filed on Sep. 5, 2003, two pages.
Supplementary European Search Report mailed on Dec. 23, 2005, for EP Application No. 03752068.1, filed Sep. 5, 2003, three pages.

* cited by examiner

*Primary Examiner*—Hope A Robinson
(74) *Attorney, Agent, or Firm*—Morrison & Foerster LLP

(57) ABSTRACT

The invention includes a process for extracting a target protein from *E. coli* cells that includes lowering the pH of a whole *E. coli* cell solution to form an acidic solution, disrupting the cells to release the protein into the acidic solution, and separating the cellular debris from the released protein to obtain a protein product enriched in the heterologous target protein. The invention also includes addition of a solubility enhancer.

13 Claims, 8 Drawing Sheets

Fig. 5
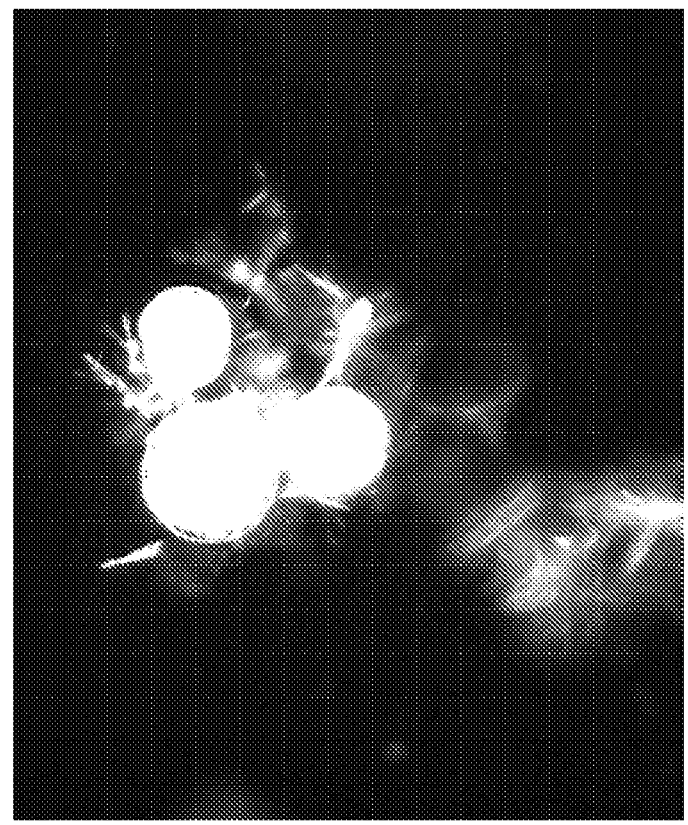
30mM MgSO$_4$
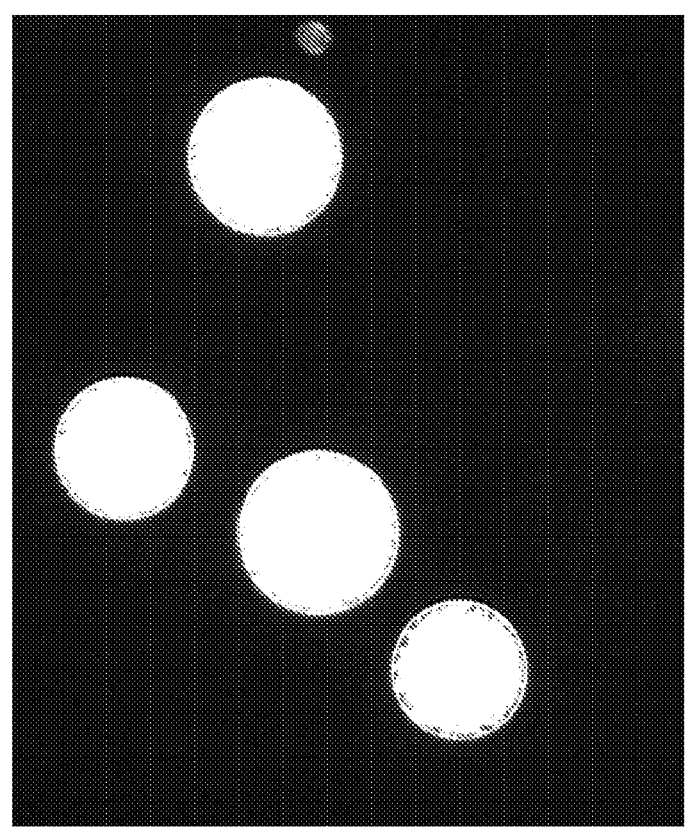
45mM MgSO$_4$

PROCESS FOR REDUCING BIOMASS-BIOMASS OR BIOMASS—RESIN INTERACTIONS

This application is a continuation of U.S. Utility application Ser. No. 10/655,874, filed Sep. 5, 2003, now U.S. Pat. No. 6,967,241, which claims priority to U.S. Provisional Application Ser. No. 60/408,653, filed Sep. 6, 2002, the disclosures of which are incorporated by reference herein.

BACKGROUND OF THE INVENTION

Biotechnological processes for producing pharmaceutical or diagnostic protein products generally employ extraction and purification steps to obtain products of interest from a variety of sources. Sources of the proteins may include bacteria, yeast, and mammalian cell culture fluids, and extracts of naturally occurring tissues, for example.

Generally, the extraction and purification steps are numerous and entail various techniques. The type of product to be produced, its intended use, and other factors influence what steps are most appropriate, what extent of purification is beneficial, and how the purification can be accomplished. In general, the greater the desired product purity, the more steps that will be utilized in the process.

Standard protein purification protocols generally begin with disruption of cells and a clarification step to remove cell and/or tissue debris from the target protein. One common way of clarifying a solution is by centrifugation. Efficiency of a centrifugation step depends on particle size, density difference between particles and surrounding liquid, viscosity of the feedstock, and the like. For solutions obtained from small cells, such as *E. coli,* the small particle size and high viscosity reduce the feed capacity during centrifugation and may interfere with the clarification process. Thus, it is often recommended to combine a centrifugation step with microfiltration. Although microfiltration can alleviate some of the problems that are encountered, fouling of the microfiltration membranes can be a further problem.

Each additional step in a protein purification process affects both the cost of the purification and the overall yield. Accordingly, manufacturers seek to obtain a desired product purity in the most economical fashion. One way to lessen the production cost is to reduce the number of steps in a purification process. Alternatively, the steps in existing processes can be modified or enhanced to reduce protein loss at each step.

One method that increases yield by eliminating process steps is expanded bed chromatography ("EBC"). EBC is a technique that utilizes an absorbent in a stable fluidized bed. When EBC is used for purifying proteins from solutions containing cell debris and/or tissue debris, prior centrifugation is not necessary. Although use of EBC eliminates a process step, both product loss and processing disadvantages can occur with EBC. The EBC apparatus maintains adsorbent in the column with a frit, and can be fouled by cell debris in the solution applied to the column. Fouling of the frit can decrease yield of product, increase processing times, and in extreme cases, render the process unusable.

Therefore, there remains a need for processes and methods that can effect higher purity protein purifications at lower costs.

SUMMARY OF THE INVENTION

The invention provides a process for extracting protein from *E. coli* cells that includes lowering the pH of a solution containing either whole or disrupted *E. coli* cells expressing a heterologous target protein, to form an acidic solution and separating cellular debris from released protein to obtain a protein product enriched in the heterologous target protein.

The invention also provides a process for extracting protein from *E. coli* cells that includes lowering the pH of a solution containing whole *E. coli* cells expressing a heterologous target protein to form an acidic solution, disrupting the cells to release protein into the acidic solution, and separating cellular debris from released protein to obtain a protein product enriched in the heterologous target protein.

The invention also provides a method as above that further includes addition of at least one solubility enhancer to either a solution of whole or disrupted *E. coli* cells expressing a heterologous target protein.

The invention also provides a method for decreasing biomass-biomass interactions, biomass-resin interactions, or a combination thereof of a solution of disrupted *E. coli* cells that includes lowering the pH of a solution containing whole *E. coli* cells expressing a heterologous target protein to form an acidic solution, and disrupting the cells to release protein in the acid solution, wherein the biomass-biomass interactions, biomass-resin interactions, or a combination thereof of the disrupted cell solution is reduced as compared with a non-acidic solution of cells that is lowered in pH after cell disruption.

The invention further provides a method for altering a flocculent in a solution of disrupted *E. coli* cells that includes lowering the pH of a solution containing whole *E. coli* cells expressing a heterologous target protein to form an acid solution, and disrupting the cells to release protein into the acidic solution, wherein moisture content of a flocculent in the released protein solution is greater when cells are disrupted in an acidic solution as compared with a non-acidic solution of cells that is lowered in pH after cell disruption.

The invention also provides a method for decreasing viscosity of a solution of disrupted *E. coli* cells that includes lowering the pH of a solution containing whole *E. coli* cells expressing a heterologous target protein to form an acidic solution, and disrupting the cells to release protein in the acid solution, wherein the viscosity of the disrupted cell solution is reduced as compared with a non-acidic solution of cells that is lowered in pH after cell disruption.

BRIEF DESCRIPTION OF THE DRAWINGS

FIG. 5 is a photograph of the interactions between an EBC resin and the homogenate with 30 mM and 45 mM $MgSO_4$.

DETAILED DESCRIPTION OF THE INVENTION

Figure 1:
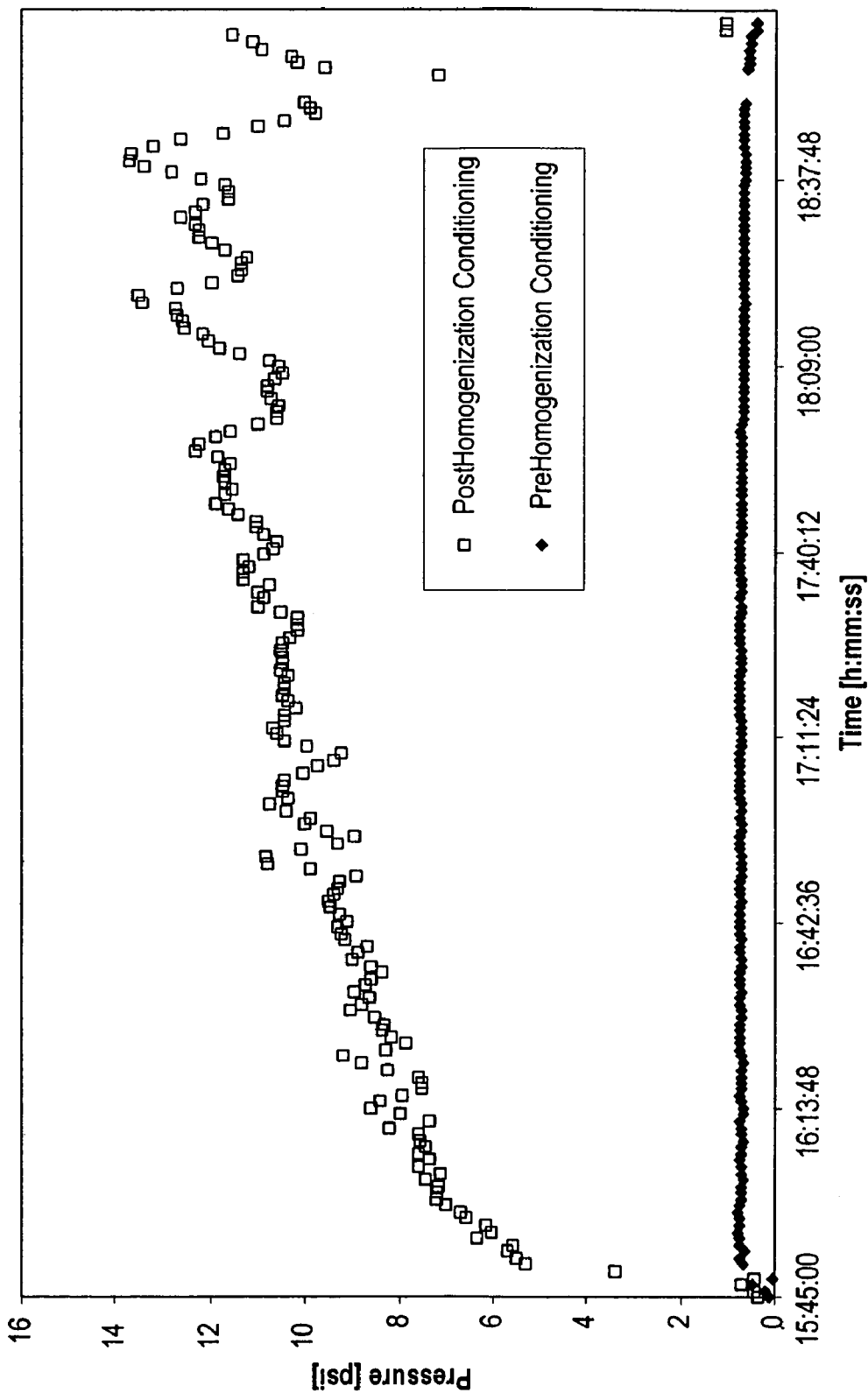
FIG. 1 is a graph comparing back pressure (psi) as a function of time for post-homogenization and pre-homogenization conditioned homogenates during EBC.

As used herein, the term "about" applies to all numeric values, whether or not explicitly indicated. The term "about" generally refers to a range of numbers that one would consider equivalent to the recited value (i.e., having the same function or result). In many instances, the term "about" may include numbers that are rounded to the nearest significant figure.

Processes of the invention are generally directed towards extracting heterologous target proteins from *E. coli* cells. As used herein, the term "heterologous target protein" refers to a recombinant protein that is not normally expressed by the host cell, tissue, or species. Examples of heterologous proteins include but are not limited to Apo2L/Trail, Fab VEGF, and Anti-Tissue Factor antibody, produced in *E. coli*. It is generally understood that a process for extracting a heterologous target protein will result in a protein product that is enriched in the heterologous target protein, but may also contain other components. Examples of such other components include, but are not limited to, proteins normally expressed by the host cell or tissue, cellular debris, and cell broth for example.

As used herein, the term "biomass" refers at least to cellular debris. "Biomass-biomass interactions" generally refer to the interactions between cellular debris that can lead to flocculation. "Biomass-resin interactions" generally refer to the interactions between cellular debris and the resin of the EBC column that can cause the cellular debris to attach to the column and may eventually contribute to fouling of the column.

As used herein, the phrase "disrupting the cells" refers to any process that releases the contents of the cell to the solution containing the cell. Examples of methods of "disrupting the cells" include but are not limited to homogenization, lysozyme, sonication, freeze-thaw, French Press, and other chemical, mechanical, or physical cell disruption methods. The process step of "disrupting the cells" may be accomplished with one or more steps, for example, multiple steps using a 4 pass homogenization.

As used herein, the step of "separating the cellular debris from the released protein" can be accomplished by a variety of known techniques. Examples of such techniques include, but are not limited to, centrifugation, microfiltration, packed bed chromatography ("PBC"), expanded bed chromatography ("EBC"), or other types of column chromatography, for example. The step of "separating the cellular debris from the released protein" does not require a complete separation of all cellular debris.

Centrifugation can be utilized to separate the cellular debris from the released protein. Any centrifugation process can be used. Specific parameters of the centrifugation would depend, at least in part, on factors such as the nature of the heterologous target protein (amino acid sequence and charge, for example), and the nature of the host cell or tissue expressing the heterologous target protein. One example of a centrifugation process that can be used is a continuous disk stack centrifuge.

EBC can be utilized to separate the cellular debris from released protein. EBC is a single pass operation in which desired proteins are purified from crude, particulate containing solution without the need for clarification, initial purification, or concentration. Although not necessary, EBC can be utilized with prior clarification, purification, or concentration steps, such as centrifugation, microfiltration, or the like.

EBC utilizes an adsorbent bed that is suspended in an equilibrium caused by the balance between particle sedimentation velocity and upward liquid flow velocity. The adsorbent expands in the bed and creates a distance between the adsorbent particles (this distance corresponds to the void volume as that term is used in chromatography techniques), that allows for relatively unhindered passage of cells, cell debris, and other particulates that may be present in the solution.

Specific methods and protocols for using EBC to separate the released protein from the cellular debris are generally known. See, for example, "Expanded Bed Adsorption, Principles and Methods", Edition AB (18-1124-26), published by Amersham Pharmacia Biotech. Specific parameters of a useful protocol would depend, at least in part, on the nature of the heterologous target protein to be separated, the host cells or tissue from which it is being separated, and other such factors.

A process of the invention includes a step of lowering the pH of a solution containing whole *E. coli* cells expressing a heterologous target protein to form an acidic solution. As used herein, "whole *E. coli* cells" refers to *E. coli* cells that have not been disrupted. As used herein, "acidic" means having a pH that is less than 7.0. The term "non-acidic" means having a pH that is 7.0 or greater.

In the process invention, the pH of the whole cell solution is preferably lowered to a pH that is about 4.0-5.0, more preferably to about 4.0-4.5. Alternatively, the pH may be lowered to no more than 4.0, and may even be lowered to about 2.0, depending on the nature of the heterologous target protein, for example.

Lowering the pH of the solution is generally accomplished by adding an acid. Any acid can be used. Preferred are those acids that have a buffering capacity at the lowered pH, for example, citric acid, acetic acid, and the like. In general, the acid will be added at a concentration of about 50 to 100 mM, but higher or lower concentrations can also be used.

It has surprisingly been discovered that lowering the pH of the whole cell solution to form an acidic solution before the cells are disrupted provides specific process and product advantages. For example, viscosity, flocculation, flow rates, processing systems, and processing times can be improved when the pH is lowered prior to disrupting the cells. The yield and quality of the heterologous target protein can also be improved when the pH is lowered prior to disrupting the cells.

Generally, the benefits of lowering the pH increase as the pH is decreased from 7. Lowering the pH before cell disruption may also serve to increase the purity of the protein product containing the heterologous protein. It is thought, but not relied upon, that lowering the pH of the whole cell solution serves to enhance the purity of the protein product by removing cell debris and whole cell contaminants from the solution after the cells have been disrupted. As the pH is lowered to an acidic pH, the purity of the heterologous target protein product generally increases. Furthermore, as the pH is lowered from pH 5 to 4, the purity of the target protein shows a more substantial increase in relation to the drop from pH 6 to 5 for example.

The process of the invention, optionally and preferably, includes addition of at least one solubility enhancer to either the whole cell solution, or the acidic whole cell solution, or the disrupted cell solution. Preferably, the at least one solubility enhancer is added to the whole cell solution prior to or contemporaneously with the lowering of the pH, more preferably prior.

Generally, the solubility enhancer is added in an amount that is effective to enhance the solubility of the heterologous target protein, and can depend, at least in part, on the nature of the heterologous target protein and the homogenate or the whole cell solution. Generally, increased amounts of solubility enhancer will increase the solubility of the heterologous target protein.

Solubility enhancers are preferably molecules that include a divalent cation, such as magnesium ($Mg^{+2}$), calcium ($Ca^{+2}$), and the like. Preferred solubility enhancers for use in a process of the invention include, but are not limited to magnesium sulfate ($MgSO_4$), magnesium chloride ($MgCl_2$), calcium sulfate ($CaSO_4$), and calcium chloride ($CaCl_2$).

The solubility enhancers are generally added in aqueous form, in an amount that results in a final concentration of from about 10 mM to about 150 mM, preferably from about 30 mM to about 120 mM.

Polyethyleneimine ("PEI") can also function as a solubility enhancer in a process of the invention. Generally, the PEI is added to the solution in an aqueous form and in an amount that results in a final concentration of about 0.1% to about 0.5% vol/vol of a 50% wt/vol solution, preferably about 0.2% to about 0.3%.

At least one solubility enhancer can be used alone, or in combination, and can be added to the process at any step, but are preferably added prior to cell disruption.

The invention also provides methods of decreasing the biomass-biomass interactions, biomass-resin interactions, or a combination thereof in a solution of disrupted E. coli cells that includes lowering the pH of the solution containing whole E. coli cells expressing a heterologous target protein to form an acidic solution, and disrupting the cells to release protein, wherein the biomass-biomass interactions, biomass-resin interactions, or a combination thereof of the disrupted cell solution is reduced as compared with a non-acidic solution of cells that is lowered in pH after cell disruption.

The level of the biomass-biomass interactions, biomass-resin interactions, or a combination thereof of a solution can also be monitored based on its effects on the process that the solution is undergoing, such as EBC, PBC, centrifugation, or microfiltration for example. These effects include but are not limited to aggregation of cell debris (also referred to as formation of homogenate or biomass or flocculation), flow rate through a column, fouling of a frit, fouling of the continuous disk-stack centrifuge, backpressure on an EBC column, or column inlet screen fouling, and the like.

The invention also provides a method for decreasing viscosity of a solution of disrupted E. coli cells that includes lowering the pH of a solution containing whole E. coli cells expressing a heterologous target protein to form an acidic solution, and disrupting the cells to release protein in the acid solution, wherein the viscosity of the disrupted cell solution is reduced as compared with a non-acidic solution of cells that is lowered in pH after cell disruption.

The viscosity may be measured by any method known to those of ordinary skill in the art, having read this specification. Examples of devices for measuring viscosity include, but are not limited to the Engler, Saybolt, and Redwood viscometers. All of the exemplary viscometers indicate the viscosity by the rate of flow of the test liquid through an orifice of standard diameter or the flow rate of a metal ball though a column of the liquid. Other types of viscometers utilize the speed of a rotating spindle or vane immersed in the test liquid. Other exemplary types of viscometers include Brookfield and Krebs-Stormer devices.

The invention also provides methods of altering a flocculent in a solution of disrupted E. coli cells that includes lowering the pH of a solution containing whole E. coli cells expressing heterologous target protein to form an acidic solution, and disrupting the cells to release protein, wherein moisture content of a flocculent in the released protein solution is greater when cells are disrupted in an acidic solution as compared with a non-acidic solution of cells that is lowered in pH after cell disruption.

As used herein, the phrase "altering the flocculent" includes changes that increase moisture content, lessen tendency for flocculant aggregation, and the like.

Another method of monitoring flocculent in a homogenate is to monitor fouling of a continuous disk-stack centrifuge. In one embodiment, this can be measured by measuring turbidity. Turbidity can be measured in NTU (National Turbidity Units).

EXAMPLES

The following Examples are offered by way of illustration and are not intended to limit the invention.

Example 1

Conditioning E. coli Cells Prior to Disruption Alters Protein Flocculation

E. coli cells containing a transgene expressing anti-VEGF antibody fragment (Rhufab V2, Chen et. al., 1999 *J. Mol. Biol.* 293: 865-881) were pre-conditioned before homogenization by lowering the pH of the cell solution to pH 4.0 via addition of 60 mM citric acid. A solubility enhancer, $MgSO_4$, was also added to the cell solution, to a concentration of approximately 120 mM. The cells were disrupted by a 4 pass homogenization with a Model HC-8000/3A homogenizer (Microfluidics Corp., Newton, Mass.) at 8000 psig, 2-8° C. After homogenization, 5 volumes of water were added to the homogenate, and the homogenate was passed through an EBC inlet screen (Multilayered SS316L, 100 μm, 1.8 mm thick, 2.5 cm diameter) (G.Bopp & Co., Zurich, Switzerland), with a flow rate of 25 ml/minute (300 cm/hr).

Control cells were similarly disrupted by a 4 pass homogenization, but with post-homogenization conditioning at pH 4.0 and without added $MgSO_4$. Acid was added to the homogenized cells, to pH 4.0 as well as $MgSO_4$ (120 mM) and 2 volumes of water. The resulting material was centrifuged to pellet insoluble material. The control supernatant was applied to the EBC inlet screen, described above. The results, shown in FIGS. 1 and 2 and in the table below, demonstrate that the pre-conditioning of E. coli cells at pH 4.0 and in the presence of $MgSO_4$ reduced biomass-biomass interaction. This reduction is demonstrated by reduced flocculation of the protein solution, as seen in the difference in backpressure, 0 psig for the pre-conditioned homogenate versus 11 psig for the post-conditioned homogenate (see Table 1, as well as FIG. 1). FIG. 1 demonstrates the pressure as a function of time for pre-homogenization conditioning and post-homogenization conditioning.

TABLE 1

| Backpressure increase on EBC outlet screen | | |
|---|---|---|
| | (L of Homogenate)/$cm^2$ | psig |
| Pre-Conditioning | >4.3 | 0 |
| Post-Conditioning | 1.7 | 11 |

Figure 2:
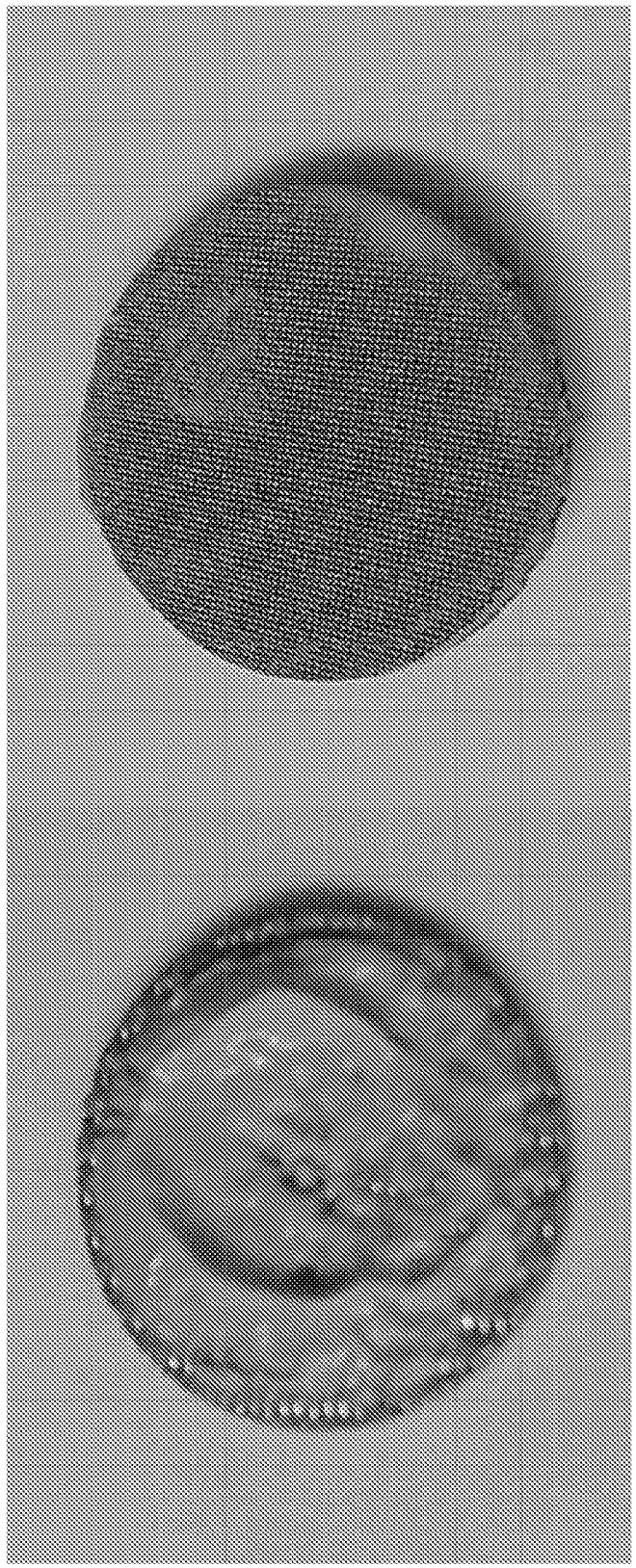
FIG. 2 is a photograph comparing fouling of a frit subjected to post-homogenization and pre-homogenization conditioned homogenates.

FIG. 2 demonstrates that the flocculated material found in the post-conditioning control is absent from the screen of the pre-conditioned sample. These results evidence a reduction of the biomass-biomass interactions when pH is reduced prior to disrupting cells to release protein.

Example 2

Conditioning of *E. coli* Cells Prior to Disruption Decreases Fouling of Continuous Disk-stack Centrifuge A pBR322-based plasmid vector was used to express a transgene expressing Fab VEGF (Chen et al., 1999, *J. Mol. Bio.*, 293: 865-881) in *E. coli* cells (strain: 60E4, genotype: W3110 DfhuA DphoA DhtrA DompT Dptr ilvG2096 DrhaR DfucP). The vector had a rop deletion to produce a higher copy number, and used the phoA promoter for transcription. Each gene contained a heat stable enterotoxin II signal sequence prior to the antibody gene for export to the periplasm. Both tetracycline and ampicillin resistances were intact on the plasmid. The fermentations were done on a 10 L scale with a fixed level of phosphate in the media such that the cells depleted phosphate as they grew, leading to induction of the phoA promoter. The *E. coli* cells were pre-homogenization conditioned by lowering the pH of the cell solution to pH 4.0 via addition of 60 mM citric acid. A solubility enhancer, $MgSO_4$, was also added to the cell solution, to a concentration of approximately 60 mM. The cells were disrupted by a 4 pass homogenization with a Model HC-8000/3A homogenizer (Microfluids, Inc.) at 8000 psig, 2-8° C. After homogenization, 2 volumes of water were added to the homogenate, and the homogenate was centrifuged in a continuous disk-stack centrifuge (Model PX205, Alfa Laval, Inc., Richmond, Va.), with a flow rate of 1.0 L/minute. The shoot rate was set to shoot once every time 60% of the bowl volume was reached.

Control cells were similarly disrupted by a 4 pass homogenization, but with post-homogenization conditioning. 60 mM citric acid was added to the homogenized cells, to pH 4.0 as well as $MgSO_4$ (60 mM) and 2 volumes of water. The resulting material was centrifuged to pellet insoluble material.

Fouling of the continuous disk centrifuge was measured as an increase in turbidity (NTU) of the centrifuged protein homogenate. The data are summarized in Table 2, and demonstrate reduced fouling (solution turbidity) of the centrifuge when cells are pre-conditioned by lowering pH and adding a solubility enhancer prior to disruption.

TABLE 2

| | Turbidity | |
|---|---|---|
| | Vol. Homogenate | NTU |
| Pre-homogenization | >1000 L | <50 |
| Post-homogenization | <100 L | >100 |

Figure 3:
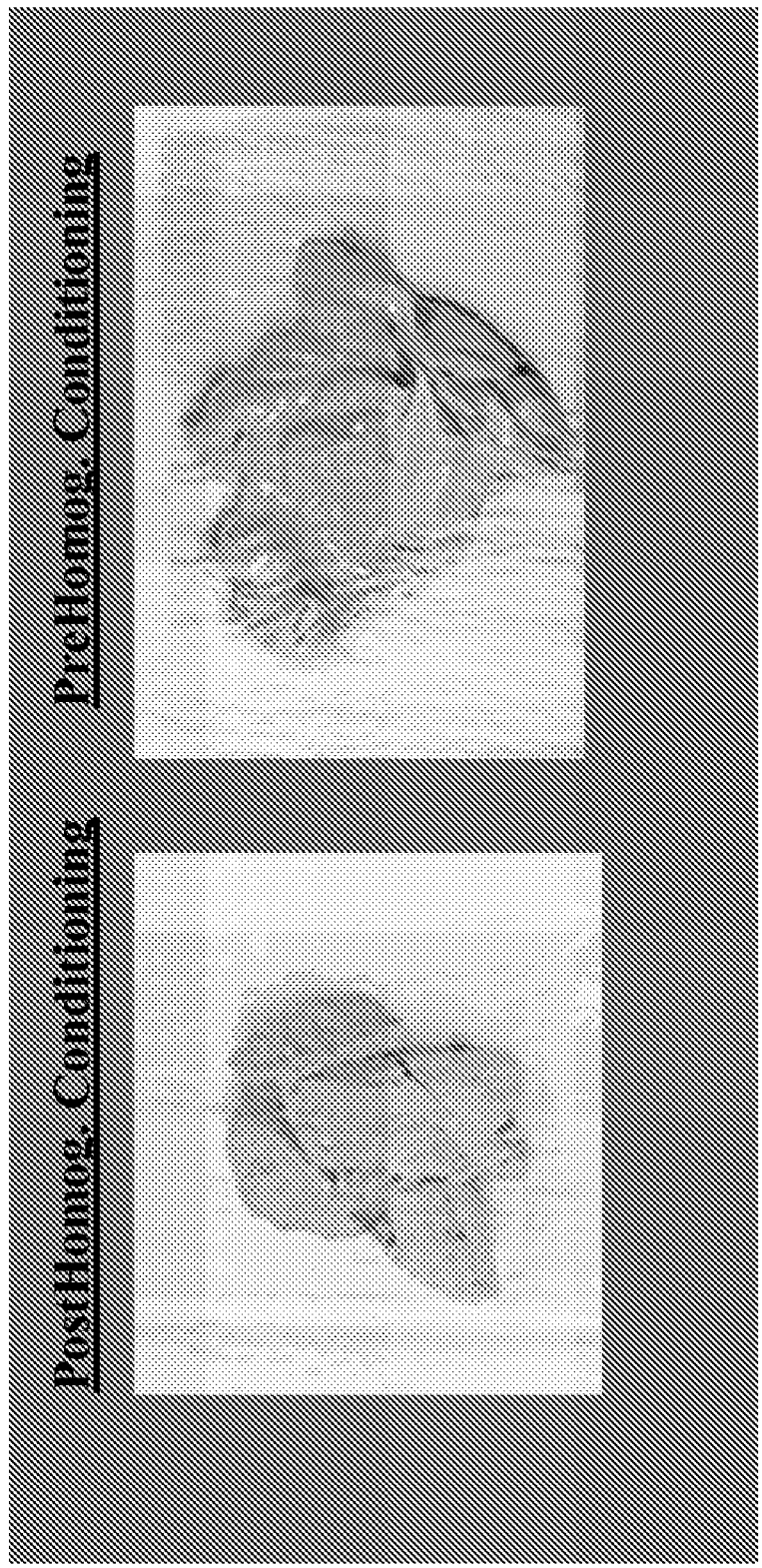
FIG. 3 is a photograph comparing pellets from centrifuged post-homogenization and pre-homogenization conditioned solutions.

FIG. 3 shows the pellet from a centrifugation in the continuous disk-stack centrifuge for pre-homogenization conditioning and post-homogenization conditioning. As can be seen in FIG. 3, the consistency of the flocculent is very different. The pellet from the pre-homogenization conditioning step appears to have more moisture content and produces a smoother "solid" than does the pellet from the post-homogenization conditioning step. These results evidence a reduction of the biomass-biomass interactions when cells are pre-conditioned prior to disruption.

Example 3

Conditioning of *E. coli* Cells Prior to Disruption Increases Flow Rate on the EBC Column To analyze the effects of pre-conditioning on flow rate, Fab VEGF homogenate obtained from pre-conditioned cells, prepared as described above in Example 1 and with control, post-conditioned homogenate were each added to SPXL Streamline (Amersham Bioscience, Inc. Piscataway, N.J.) EBC columns (2.6 cm diameter×100 cm high) with a resin settled bed height of 30 cm, and an expanded bed height of 90 cm. The EBC columns were each equipped with an EBC inlet screen (Multilayered SS316L, 100 µm, 1.8 mm thick, 2.5 cm diameter). The flow rate of the homogenates through the columns were compared to each other using buffer as a control. The pre- and post-homogenization conditioning samples were prepared at conditioning pH 4.5, 5.0, 5.5, 6.0, and 6.5.

Figure 4:
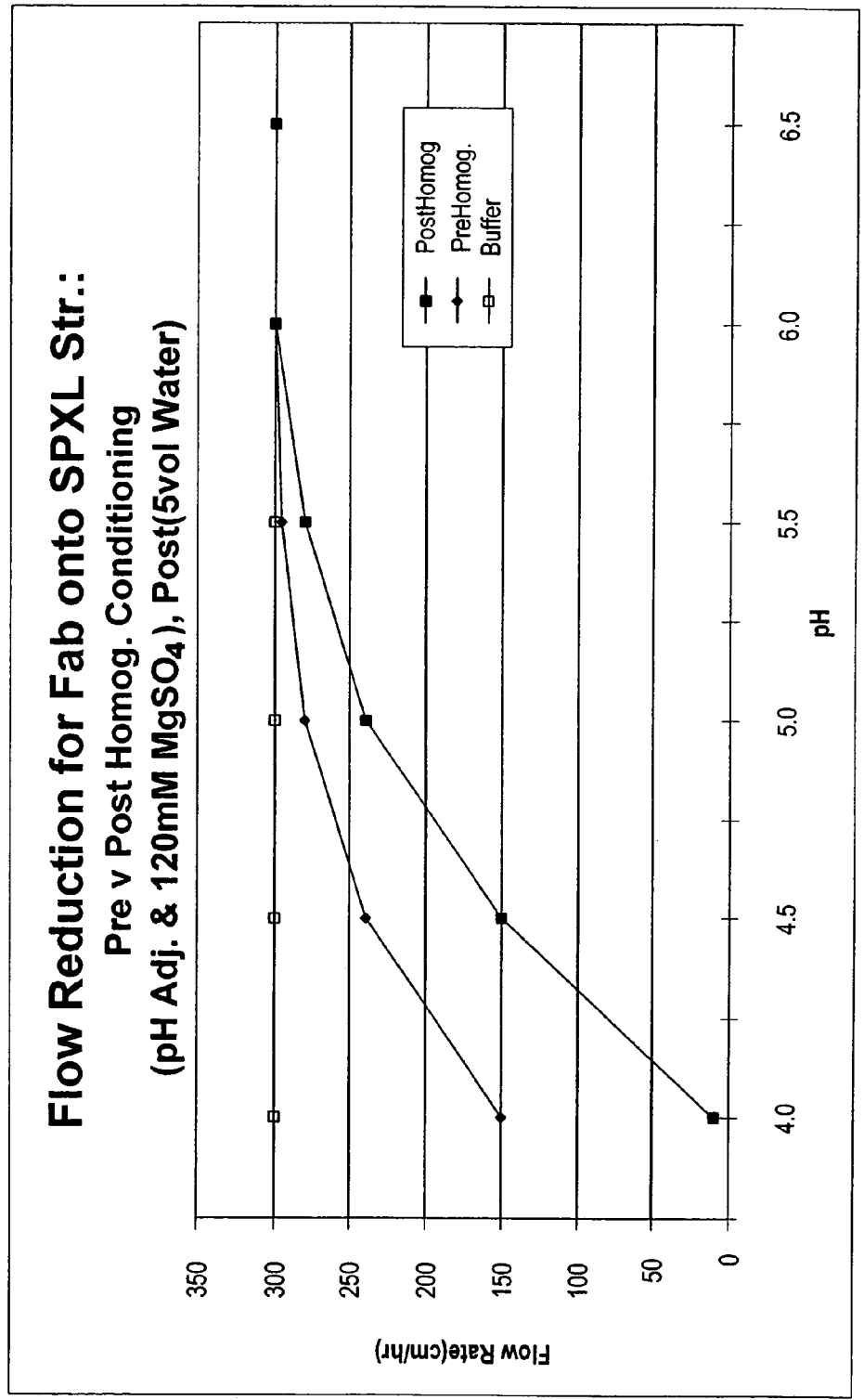
FIG. 4 is a graph of the flow rate (cm/hr) for EBC of a post-homogenization conditioned homogenate, a pre-homogenization conditioned homogenate, and a buffer solution at pH ranging from 4.0 to 6.5.

The results are depicted in FIG. 4, and demonstrate that pre-homogenization conditioning resulted in an increased flow rate through the EBC column. The flow rate also increased as the pH is lowered. These results evidence a reduction of the biomass-biomass interactions as well as a reduction of the biomass-EBC resin interactions, and indicate better flow rates obtained with pre-conditioning.

Example 4

Effect of Concentration of Solubility Enhancer on Biomass-Resin Interactions

*E. coli* cells (strain: 43E7, genotype: W3110 DfhuA phoADE15 D(argF-lac) 169 ptr3 degP41 DompT (DnmpC-fepE) ilvG2096) containing a transgene expressing Apo2L (Pitlie et al., 1996, *J. Bio. Chem.*, 271: 12687-12690) were used to express protein. A pBR22-based plasmid vector with a phoA promoter driving transcription was used for the expression. The plasmid contained 3 tRNA genes for enhanced production and had both tetracycline and ampicillin resistances intact. The cells were disrupted by a 4 pass homogenization with a Model HC-8000/3A homogenizer (Microfluids, Inc.) at 8000 psig, 2-8° C.

The homogenate was conditioned by addition of a solubility enhancer, $MgSO_4$, to a concentration of approximately 45 mM or 30 mM. Two (2) volumes of water were added, and the pH of the homogenate was adjusted to pH 6.5 via addition of 60 mM citric acid. The conditioned homogenate was run through an EBC column (2.5 cm diameter×210 cm high) containing SP Streamline (Amersham Bioscience, Inc.) with a resin settled bed height of 65 cm, and an expanded bed height of 195 cm. The EBC column was equipped with an EBC inlet screen (Multilayered SS316L, 100 µm, 1.8 mm thick, 2.5 cm diameter) (Amersham Bioscience, Inc). The flow rate in the column was 200 cm/hour.

FIG. 5 shows photographic images of the resin taken from the top screen after the storage phase demonstrates a difference in the resin-biomass interactions in the two homogenate solutions in the EBC column conditioned with differing amounts of $MgSO_4$. The homogenate conditioned with the higher concentration of $MgSO_4$ (45 mM) showed less resin-biomass interactions than that conditioned with 30 mM $MgSO_4$, which showed much greater aggregation of the resin.

Example 5

Effect of Concentration of Solubility Enhancer on Protein Solubility

E. coli cells (strain: 60H4, genotype: W3110 DfhuA phoADE15 D(argF-lac) 169 degP41 deoC Dprc spr DmanA) containing a transgene expressing Anti-Tissue Factor antibody (Presta et al., 2001, Thromb. Haemost., 85: 379-89) were disrupted by a 4 pass homogenization with a Model HC-8000/3A homogenizer (Microfluids, Inc.) at 8000 psig, 2-8° C. The homogenate was conditioned by addition of two solubility enhancers, PEI at various concentrations and $MgSO_4$, to a concentration of 0 mM, 10 mM, 20 mM, 30 mM, 40 mM, or 50 mM. The pH of the solution was adjusted to pH 4.0 via addition of citric acid and 2 volumes of water were added to the adjusted solution. The homogenate was centrifuged to remove solids, and the supernatant was added to a Porous-G affinity column (Perceptives Biosystems). Protein was eluted from the column with low pH buffer and quantitated.

Figure 6:
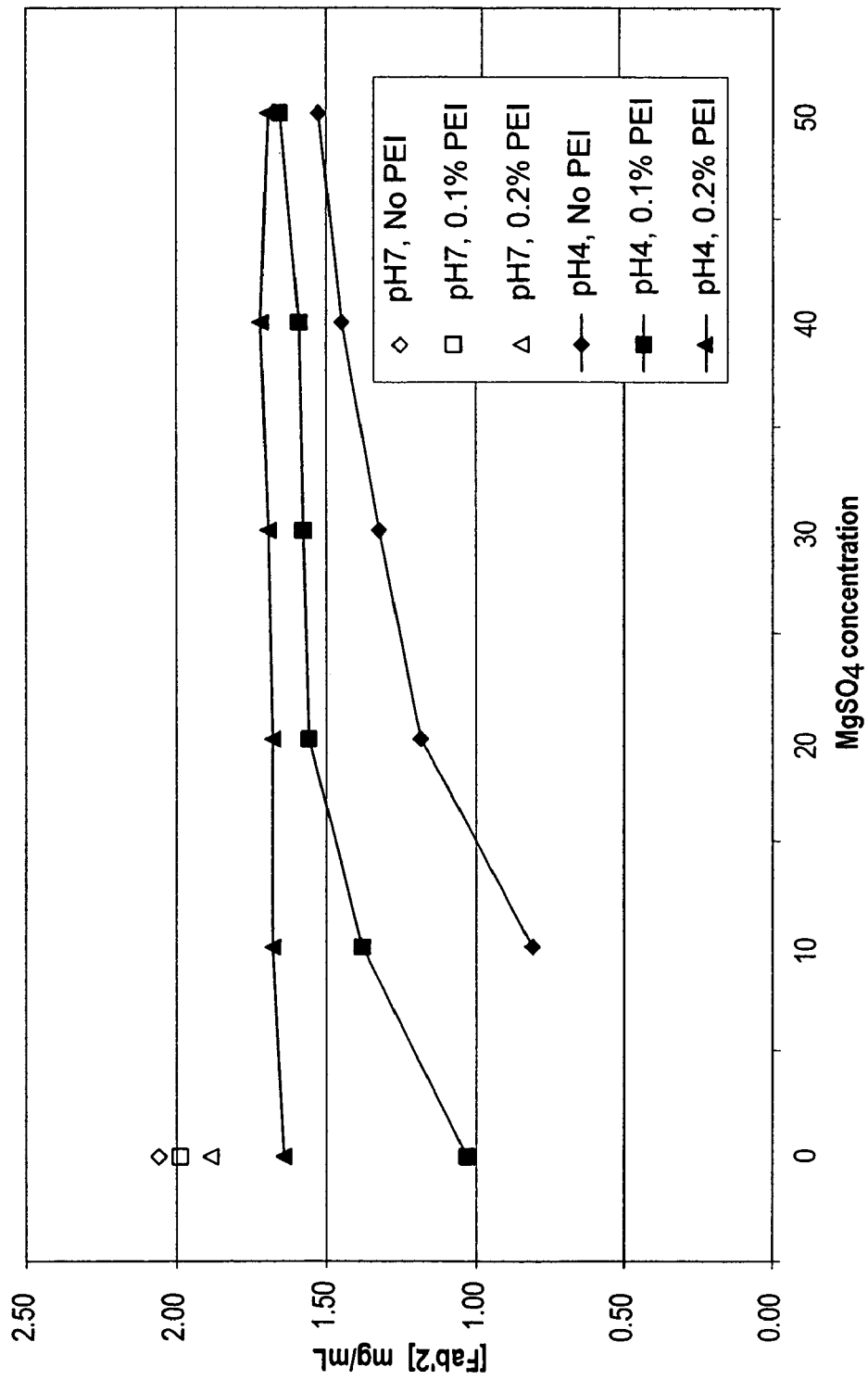
FIG. 6 is a graph of the concentration (mg/mL) of Fab'2 in solutions with variable concentrations of $MgSO_4$ and polyethyleneimine.

FIG. 6 shows the concentration of Anti-Tissue Factor antibody protein in the supernatant for each of the test samples. These results generally show that as the amount of the solubility enhancer, $MgSO_4$ or PEI, was increased, more protein was obtained.

Example 6

Effect of Concentration of Solubility Enhancer on EBC Resin Capacity

E. coli cells containing a transgene expressing Apo2L /TRAIL (Ashkenazi et al., 1999, J. Clin. Invest., 104: 155-162) were disrupted by a 4 pass homogenization with a Model HC-8000/3A homogenizer (Microfluids, Inc.) at 8000 psig, 2-8° C. After homogenization, the homogenate was conditioned through addition of a solubility enhancer, $MgSO_4$, to a concentration of 10 mM, 20 mM, or 40 mM. A control homogenate contained no $MgSO_4$. Next, the pH of the homogenate was adjusted to pH 6.5 via addition of 60 mM citric acid, and 2 volumes of water were added to the adjusted solution. The conditioned homogenate was then mixed with 1 mL of EBC resin, SP Streamline (Amersham Bioscience, Inc.) in a 15 mL conical plastic screw cap tube, in excess of the conditioned homogenate.

Figure 7:
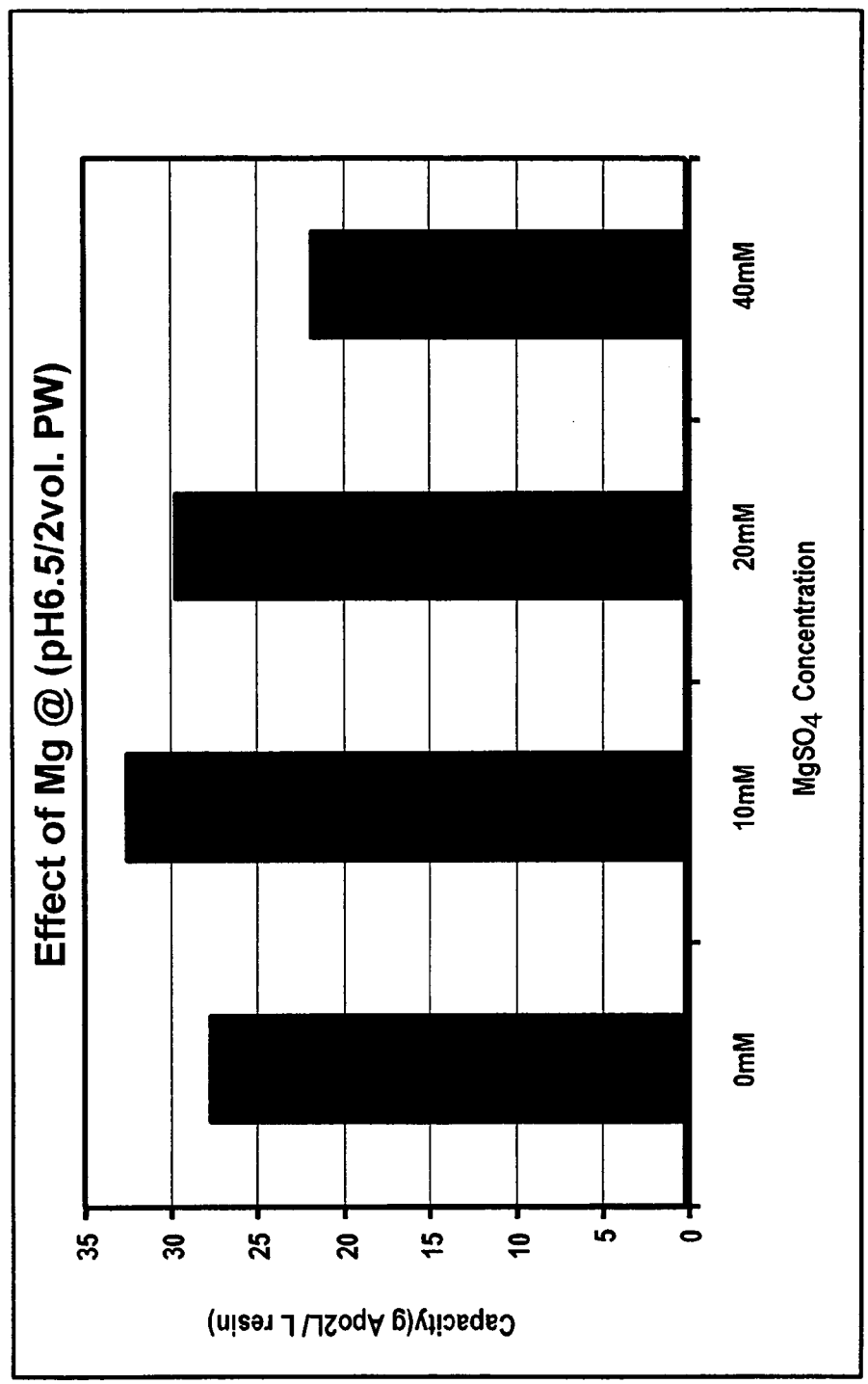
FIG. 7 is a bar graph of the capacity (g Apo2L/L resin) of the resin for Apo2L protein at various concentrations of $MgSO_4$.

The capacity of the resin for each of the conditioned homogenate solutions was determined, and the data is shown in FIG. 7. The presence of the solubility enhancer, $MgSO_4$, increased the capacity of the resin for Apo2L at 10 mM and 20 mM. However, as the concentration of the $MgSO_4$ continued to increase (40 mM), the resin capacity decreased. This decrease may be due to the increased conductivity of the solution with increased concentrations of $MgSO_4$.

Example 7

Effect of pH Adjustment on Protein Purity

E. coli cells containing a transgene expressing Anti-Tissue Factor antibody were disrupted by a 4 pass homogenization with a Model HC-8000/3A homogenizer (Microfluids, Inc.) at 8000 psig, 2-8° C. The homogenate was conditioned through addition of PEI at 0.2%. Various salts were also added, including the solubility enhancer, $MgSO_4$ at 100 mM, NaCl at 250 mM, and $Na_2SO_4$ at 100 mM. The pH of the solution was adjusted to pH 4.0, 5.0, 6.0, or 7.0 by addition of citric acid and 2 volumes of water were added. The homogenate was centrifuged and the supernatant was subjected to SDS-PAGE analysis at 10% Bis-Tris/MOPS (Novex, Inc.) with Coomassie Blue staining.

Figure 8:
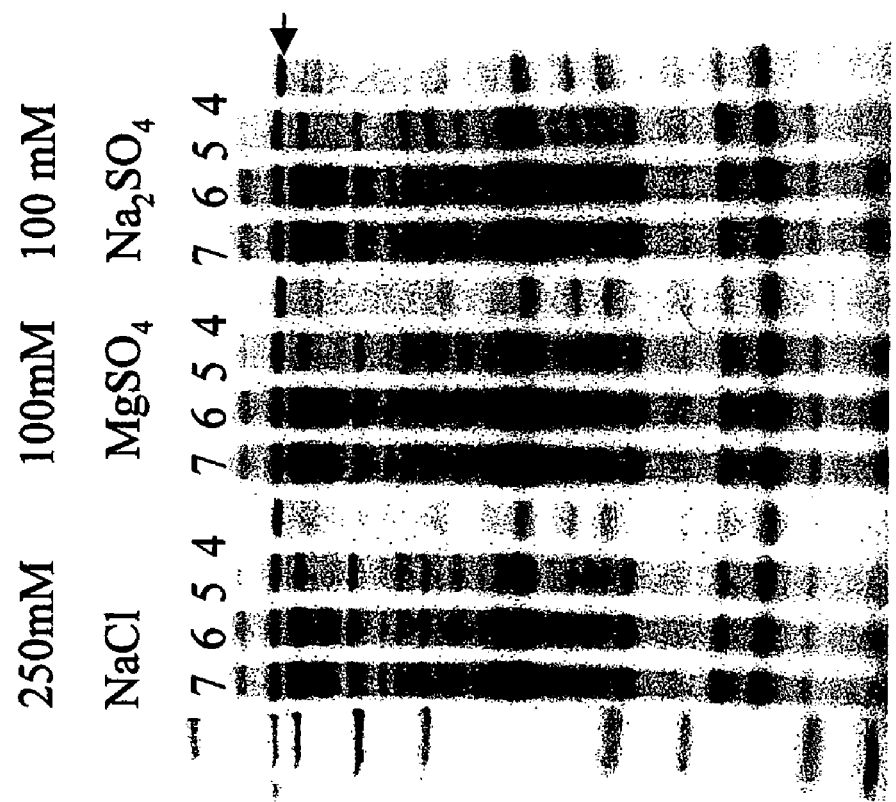
FIG. 8 is an SDS-PAGE gel of Anti-Tissue Factor homogenates at pH from 4 to 7 that include either a solubility enhancer or various salts.

FIG. 8 is an electrophoretic gel showing the resulting protein products. The gel demonstrates that as the pH of the cell homogenate was decreased from 7.0 to 4.0, the amount of contaminating protein (that is, protein other than the heterologous protein, Anti-Tissue Factor antibody) present in the homogenate decreased. A dramatic enrichment of the desired heterologous protein product in the E coli cell homogenate occurred when the pH was dropped from 5.0 to 4.0.

Example 8

Effect of pH Adjustment on Protein Purity

E. coli cells containing a transgene expressing Anti-Tissue Factor were disrupted by a 4 pass homogenization with a Model HC-8000/3A homogenizer (Microfluids, Inc.) at 8000 psig, 2-8° C. The homogenate was conditioned by addition of two solubility enhancers, PEI at 0.2% and $MgSO_4$, at 100 mM. The pH of the solution was adjusted to pH 4.0, 5.0, 6.0, or 7.0 by addition of citric acid and 2 volumes of water were added. The homogenate was centrifuged and the supernatant was subjected to HPLC using a Protein G column (Perceptive Biosystems, Inc.) with a Bradford staining reagent (Pierce Chemical Co., Rockford, Ill.). The data are shown below in Table 3, and demonstrate a higher fold increase in protein purity when the protein was produced from a homogenate conditioned at acidic pH.

TABLE 3

| pH | Brad (g/L) | ProG (g/L) | ProG/Brad | Purity Increase (pH/pH 7) |
|---|---|---|---|---|
| 4.0 | 8.5 | 2.12 | 0.250 | 5.0 fold |
| 5.0 | 25.3 | 2.28 | 0.090 | 1.7 fold |
| 6.0 | 36.9 | 2.35 | 0.064 | 1.2 fold |
| 7.0 | 45.0 | 2.33 | 0.052 | — |

Example 9

Comparison of EBC Using a Solubility Enhancer and PBC Without Solubility Enhancer Packed bed chromatography purification was carried out as follows. E. coli cells containing a transgene expressing Apo2L/Trail were subjected to a 4 pass homogenization with a Model HC-8000/3A homogenizer (Microfluids, Inc.) at 8000 psig, 2-8° C. After homogenization, two volumes of water were added and polyethyleneimine was also added to result in a final concentration of 0.3% by weight. The homogenate solution was then centrifuged in a continuous disk-stack centrifuge (Model PX205, Alfa Laval, Inc.), with a flow rate of 1.0 L/minute. The supernatant was purified on a SP SEPHAROSE ™ FF column (2.5×20cm) (Amersham Biosciences).

The EBC purification was carried out as follows. E. coli cells containing a transgene expressing Apo2L/Trail were subjected to a 4 pass homogenization with a Model HC-8000/3A homogenizer (Microfluids, Inc.) at 8000 psig, 2-8° C. After homogenization magnesium sulfate ($MgSO_4$) was added to a final concentration of 30 mM, two volumes of water were added, and the pH of the solution was adjusted to pH 6.5. The homogenate was then subjected to EBC with a SP Streamline (Amersham Bioscience, Inc.) adsorbent in a (2.5× 65) cm column and a (2.5×14 cm) column.

Table 4 below compares the recovery of Apo2L/Trail from the three processes.

TABLE 4

| Technique | Percent Recovery | | | |
|---|---|---|---|---|
| | Extraction | Cent. | Chrom. | Overall |
| Packed (SPFF) 2.5 cm diameter | 84% | 88% | 95% | 70% |
| Expanded (SP Str.) 2.5 cm diam. | | | 95% | 95% |
| Expanded (SP Str.) 14 cm diam. | | | 94% | 94% |

The EBC protocols utilized above resulted in the same flow rate (200 cm/hour) and the same load volume (2 volumes of water) as the PBC protocol; therefore, there was no loss in overall load process time, which was 4.5 hours. The addition of $MgSO_4$ as a solubility enhancer served to enhance the solubility of the Apo2L/Trail as the pH was decreased from 7.5 to 6.5, thereby increasing the EBC resin capacity. The $MgSO_4$ reduced the homogenate-resin interactions such that the low density resin aggregate formation was minimized during the EBC load phase, thereby increasing protein recovery.

Example 10

Comparison of Packed Bed Chromatography and Expanded Bed Chromatography with Homogenate Conditioning The packed bed chromatography (PBC) purification was carried out as follows. E. coli cells containing a transgene expressing Apo2L/Trail were subjected to a 4 pass homogenization with a Model HC-8000/3A homogenizer (Microfluids, Inc.) at 8000 psig, 2-8° C. After homogenization, two volumes of water were added and polyethyleneimine was added to a final concentration of 0.3% by weight. The solution was then centrifuged in a continuous disk-stack centrifuge (Model PX205, Alfa Laval, Inc.), with a flow rate of 1.0 L/minute. The supernatant was purified on a SP SEPHAROSE™ FF column (2.5×20) cm (Amersham Biosciences).

The expanded bed chromatography (EBC) purification was carried out as follows. E. coli cells containing a transgene expressing Apo2L/Trail were subjected to a 4 pass homogenization with a Model HC-8000/3A homogenizer (Microfluids, Inc.) at 8000 psig, 2-8° C. $MgSO_4$ was added to the homogenate to obtain a final concentration of 30 mM $MgSO_4$. The pH of the solution was also adjusted to pH 6.5 and five volumes of water were added. The homogenate was then subjected to EBC with a SP Streamline adsorbent (Amersham Biosciences, Inc.) in a (2.5×30) cm column and a (2.5×14)cm column.

Table 5 below compares the recovery of FAB V2 (AMD) from the three processes.

TABLE 5

| Technique | Percent Recovery | | | |
|---|---|---|---|---|
| | Extraction | Cent. | Chrom | Overall |
| Packed (SPFF) 2.5 cm diameter | 90% | 86% | 97% | 75% |
| Expanded (SP Str.) 2.5 cm diam. | | | 96% | 96% |
| Expanded (SP Str.) 14 cm diam. | | | 97% | 97% |

Although the EBC protocol utilized above resulted in a total load time that was 4 times longer than that of the PBC protocol (24 hours versus 6 hours), protein recovery was greatly increased using EBC. $MgSO_4$ served to reduce both homogenate-homogenate and homogenate-resin interactions, and thereby enhanced the processing parameters of the EBC protocol. Adjustment of the pH before homogenization (pre-conditioning) also aided processing by reducing homogenate-homogenate interactions, further increasing protein yields (data not shown).

The above specification, examples and data provide a complete description of the manufacture and use of the composition of the invention. Since many embodiments of the invention can be made without departing from the spirit and scope of the invention, the invention resides in the claims hereinafter appended.

The specification includes references to numerous patent and literature citations. Each is hereby incorporated by reference for all purposes, as if fully set forth.

I claim:

1. A process for reducing biomass-biomass interactions, biomass-resin interactions, or a combination thereof, comprising:
   a) preconditioning whole *Escherichia coli* cells by lowering the pH of a solution containing whole *Escherichia coli* cells to form an acidic cell solution having a pH of 4.0 to 5.0 and adding at least one solubility enhancer to the acidic cell solution containing the whole *Escherichia coli* cells, wherein the solubility enhancer comprises a divalent cation or polyethyleneimine; and
   b) disrupting the preconditioned whole cells to release protein into the acidic solution; wherein the preconditioned-protein-containing disrupted cell solution exhibits reduced flocculation, turbidity, and/or aggregation with a chromatography resin as compared with a non-preconditioned control.

2. The process of claim 1, wherein the pH is lowered to 4.0 to 4.5.

3. The process of claim 2, wherein the pH is lowered to no more than 4.0.

4. The process of claim 1, wherein the at least one solubility enhancer comprises a divalent cation.

5. The process of claim 1, wherein the at least one solubility enhancer is magnesium sulfate or polyethyleneimine.

6. The process of claim 1, wherein the at least one solubility enhancer comprises a divalent cation and polyethyleneimine.

7. The process of claim 4, wherein the divalent cation is added at a concentration of 10 mM to 150 mM.

8. The process of claim 5, wherein the polyethyleneimine is added at a concentration of 0.2% to 0.3% vol/vol of a 50% wt/vol solution.

9. The process of claim 4, wherein the divalent cation comprises magnesium or calcium.

10. The process of claim 4, wherein the divalent cation is added at a concentration of 30 mM to 120 mM.

11. The process of claim 5, wherein the polyethyleneimine is added at a concentration of 0.1% to 0.5% vol/vol of a 50% wt/vol solution.

12. The process of claim 1, wherein said step of lowering the pH comprises adding acid at a concentration of 50 mM to 100 mM.

13. The process of claim 12, wherein the acid is citric acid or acetic acid.

* * * * *

UNITED STATES PATENT AND TRADEMARK OFFICE
CERTIFICATE OF CORRECTION

PATENT NO.       : 7,662,934 B2                                         Page 1 of 1
APPLICATION NO.  : 11/264300
DATED            : February 16, 2010
INVENTOR(S)      : Richard L. Gehant It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 287 days.

Signed and Sealed this

Thirtieth Day of November, 2010

David J. Kappos
*Director of the United States Patent and Trademark Office*